United States Patent [19]

Stead et al.

[11] Patent Number: 4,975,284
[45] Date of Patent: Dec. 4, 1990

[54] CONTROLLED RELEASE MEANS

[75] Inventors: James A. Stead; Shore Nabahi, both of Swindon, Great Britain

[73] Assignee: Roussel Uclaf, Paris, France

[21] Appl. No.: 221,316

[22] Filed: Jul. 19, 1988

[30] Foreign Application Priority Data

Jul. 21, 1987 [GB] United Kingdom ................ 8717168

[51] Int. Cl.$^5$ ............................................. A61K 9/22
[52] U.S. Cl. .................................. 424/497; 424/494
[58] Field of Search ....................... 424/497, 473, 494; 604/892.1

[56] References Cited

U.S. PATENT DOCUMENTS

4,684,524  8/1987  Eckenhoff et al. ............. 424/473 X
4,685,918  8/1987  Amidon et al. .................. 424/473 X
4,687,660  8/1987  Baker et al. ...................... 424/473 X
4,801,461  1/1989  Hamel et al. .................... 424/473 X

Primary Examiner—Thurman K. Page
Attorney, Agent, or Firm—Bierman and Muserlian

[57] ABSTRACT

A controlled release means comprisng a core of at least one water-soluble ingredient of which at least one ingredient is to be released in a controlled manner, said core being surrounded by a semi-permeable membrane coating containing dispersed water-soluble pore-forming particles in sufficient amount to give rise to dissolution upon exposure to an aqueous environment to form only one or two pores extending through the coating to provide communication between the core and the exterior of the coating and a method of making the same.

7 Claims, 9 Drawing Sheets

CONTROLLED RELEASE MEANS

STATE OF THE ART

U.S. Pat. Nos. 3,845,770 and 3,916,899 describe a means for releasing a beneficial agent in which the beneficial agent is surrounded by a semi-permeable membrane through which is provided a passageway. In operation, the means is placed in an external fluid which permeates or diffuses through the membrane and dissolves the beneficial agent. An osmotic pressure gradient across the membrane is thereby established with the result that the solution of beneficial agent is discharged through the passageway into the surrounding fluid. These means are primarily intended for pharmaceutical use as single-entity dosage forms, e.g. tablets coated with a semi-permeable membrane.

Single-entity forms are generally considered less suitable as sustained-release agents since they have a characteristic propensity of becoming stuck at various places in the gastrointestinal tract. In such a case, it will be appreciated that release of the active ingredient would occur in a very localized area, and the active ingredient itself might not then be conveyed to its desired site of activity. Moreover, the presence of such high concentrations of active ingredient in one discrete area of the body would be likely to give rise to local irritation.

Single-entity dosage forms which rely on coatings to achieve a modified release are also particularly vulnerable to rupturing, and in the event of rupture, a similar massive local release of active ingredient would be expected to ensue. A further disadvantage of single-entity forms is their dependence on stomach-emptying times and in general, a tablet or the like would tend to be retained in the stomach until being swept away involuntarily by so-called "housekeeper" waves.

In the means described in the said U.S. Patents, one way in which it is envisaged that the passageway or pore can be formed in the semi-permeable membrane is by drilling during assembly of the means. In a related device disclosed in U.S. Pat. No. 4,278,087, it is envisaged that the drilling can be effected by a laser. While laser drilling can be executed with ease and precision on single-entity forms such as tablets, it is however much more difficult and hence time-consuming in practice to achieve a correspondingly successful result with the much smaller pellets commonly employed in multiparticulate compositions. In any event, the very fact that the aforementioned devices require a hole to be formed, for example by drilling, in the membrane coating before use represents in itself a significant drawback.

Attempts have been made in EP-A-0,171,457 to overcome this deficiency by the provision of means whereby pores in the membrane can be generated in situ. In essence, water-soluble granules are dispersed throughout the semi-permeable membrane. Upon placing the resulting composition in an aqueous environment, the granules dissolve and thereby give rise to the required pores. EP-A-0,169,105 describes a similar device.

However, the ratio of pore-forming material to semi-permeable coating material in EP-A-0,169,105 and EP-A-0,171,457 is high, giving rise to a multiplicity of pores or in the case of EP-A-0,169,105, to a network of discontinuous interwoven channels interconnected via tortuous paths and distributed throughout the membrane coat. Such a preponderance of pores in the coating would suggest that release of active ingredient from these compositions should be predominantly diffusion-controlled.

The results quoted in EP-A-0,169,105 and EP-A-0,171,457 show that complete release of active ingredient from the specific compositions disclosed therein occurs over a relatively short space of time. Thus, while adequate controlled release of active ingredient over an extended time period might in principle be possible with the highly porous compositions disclosed therein if compositions used were large single-entity dosage forms, it seems unlikely that such control could be achieved with the much smaller pellets customarily present in multiparticulate compositions.

OBJECTS OF THE INVENTION

It is an object of the invention to provide a means for the uptake of external fluid and concomitant release of active ingredient to be regulated predominantly by osmosis, since osmotic control is subject to zero-order kinetics and thereby maintains a far more constant rate of release of active ingredient over an extended time period than does diffusion control.

It is another object of the invention to a process for preparing a controlled release means.

These and other objects and advantages of the invention will become obvious from the following detailed description.

THE INVENTION

The novel controlled release means of the invention is comprised of a core of at least one water-soluble ingredient of which at least one ingredient is to be released in a controlled manner, said core being surrounded by a semi-permeable membrane coating containing dispersed water-soluble pore-forming particles in sufficient amount to give rise to dissolution upon exposure to an aqueous environment to form only one or two pores extending through the coating to provide communication between the core and the exterior of the coating.

By suitable choice of conditions under which coating is carried out, it is possible to obtain one, or at most two, pore(s) per means, for most (ca. 75%) of the devices. This restriction in the number of pores ensures that delivery of the water-soluble ingredient(s) occurs by osmotic control which means that zero-order release can be maintained over an extended time period and the desired ingredient thereby delivered at a constant, controlled rate. This is in contrast to EP-A-0,169,105 wherein as mentioned above, the reticulate, highly porous membrane permits rapid total release of active ingredient over a relatively short time-scale in an apparently diffusion-controlled process.

The means may, for example, be a pellet, e.g. a pellet forming a component of a multiparticulate composition.

It will be appreciated that the pore or pores should be sufficiently small to ensure that influx of water through the coat to the core occurs substantially by osmosis with the required osmotic gradient arising from dissolution of the water-soluble ingredient(s) within the core, but sufficiently large to ensure that premature rupturing of the coat resulting from an excessive build-up of pressure within the device is prevented.

In use, each water-soluble particle in the coat dissolves and thereby provides a delivery pore. Meanwhile, water penetrates into the core through the semi-permeable membrane, whereupon the core constituents dissolve in the water and generate an osmotic pressure within the core. This then results in delivery of the dissolved ingredient(s) to the exterior through the pore formed by dissolution of the water-soluble particles in the coat.

As mentioned above, the means of the invention may be presented as components of a multiparticulate composition. Thus, according to a further feature of the present invention there are provided compositions comprising a plurality of controlled release devices of the invention.

As discussed earlier, a sustained-release pharmaceutical formultation when presented in the form of a multiparticulate composition benefits from such advantages as the distribution of the dose over many individual particles, the gradual emptying of the particles with the food from the stomach leading to a significant distribution of the dosage units throughout the gastrointestinal tract and a consequent minimization of the possibility of localized side effects such as irritation which might arise from certain drugs.

The means of the invention can be produced in the form of pellets by coating appropriate pellet cores with a semi-permeable material containing pore-forming agent dispersed therein. The amount of pore-forming agent required to yield an average of one or two pore-forming particles per pellet can be calculated from the number of pellet cores per unit mass to be coated and the number of particles of pore-forming agent per unit mass. These quantities can in turn be readily calculated from available data regarding the particle size and density of the pellet cores and particles of pore-forming agent.

For a given number of pellets x, the number of particles of pore-forming agent will be between x and 2x in the effective portion of the solution of coating material. If it is desired to maximize the number of pellets containing a single pore-forming particle in the coating, then the number of pore-forming particles in the effective portion of the coating material solution will be x. The expression "effective portion" as used herein signifies that proportion of coating material which directly contributes to the thickness of the coating on the pellet cores since in practice, some of coating material and particles of pore-forming agent onto the walls and associated regions of the coating apparatus is encountered. Thus, for a given thickness of coating material, the weight ratio of pore-forming agent to coating material can be precisely determined from considerations of particle size and density discussed above.

Accordingly, the proportion by weight of pore-forming agent to coating material in the finished pellet is typically between 1 to 40 and 1 to 6000, but is preferably about 1 to 300.

It will be appreciated that the coating material should not appreciably cover the particles of pore-forming agent. For this reason, it is preferred that the diameter of the particles of pore-forming agent exceeds the thickness of the coat; nevertheless, the reverse condition (i.e. thickness of coat greater than diameter of pore-forming particle) need not be ruled out, provided that the requirement that, upon dissolution of the water-soluble particle, the resulting pore permits a direct means of egress for the dissolved core constituents to the pellet exterior is complied with.

The coating operation may conveniently be carried out using a rotating pan or a fluidized bed coater. Standard coating procedures such as those described, for example, in Remington's Pharmaceutical Sciences, 16th Edition, 1980 may conveniently be used.

Another feature of the invention provides a method of preparing controlled-release devices comprising coating appropriate cores with a semi-permeable material, the coating operation being effected in the presence of an appropriate quantity of pore-forming particles whereby, for the majority of the means obtained, the coat has dispersed therein water-soluble particle(s) in an amount sufficient to give rise by dissolution, upon placing the device in an aqueous environment, to form one or two pores, preferably one pore, extending through the coat enabling communication between the core and the exterior of the device.

Another feature of the invention provides a multiparticulate controlled-release compositon comprising a plurality of means, each means having a core comprising one or more water-soluble ingredients, at least one of said water-soluble ingredients being the ingredient which it is desired to release in a controlled manner and each core being surrounded by a semi-permeable membrane coat, wherein a majority (advantageously at least 75%) of the means have dispersed in the semi-permeable membrane coat water-soluble particle(s) of such a number as to give rise by dissolution, upon placing the means in an aqueous environment, to one or two pores, preferably one pore, extending through the coating enabling communication between the core and the exterior.

As will be readily appreciated, the controlled-release means of the invention can be used in a wide variety of applications. It will be of use wherever there is a requirement for a means whereby a water-soluble ingredient can be controllably released into an aqueous environment over an extended period of time. Typical examples of fields in which it finds particular favor include human and veterinary medicine, and agriculture. In the latter case, the means might advantageously be adapted for use in, for example, the controlled discharge of pesticides, water-soluble fertilisers and/or soil trace elements or minerals. However, the means of the invention are of particular use in human medicine and will be further described with particular reference to that use.

As mentioned previously, the means of the invention may take the form of pellets, e.g. pellets presented in the form of multiparticulate compositions and the invention will be further described with particular reference to pellets.

Coating materials which may conveniently be used include cellulose acetate, cellulose acetate propionate and cellulose acetate butyrate. Other polymers such as, for example, polyvinyl chloride, polyvinyl chloride/vinyl acetate copolymers, polyurethanes, polystyrenes, polyvinyl acetate and/or polyacrylic acid esters may also be used for coating purposes. The semi-permeable membrane may, if desired, additionally contain small quantities of plasticizer such as, for example, PEG 400 or dibutyl phthalate.

Solvents which may conveniently be used for coating include, for example, acetone, methyl ethyl ketone, methylene chloride, methanol and combinations of acetone and methyl ethyl ketone.

Materials which typically may be utilized as the pore-forming agent include, for example, crystals of sucrose, mannitol or sorbitol, or salts such as, for example, sodium chloride or potassium chloride. The particles of pore-forming agent, which should be substantially insoluble in the solvent used for coating, are conveniently between 10 and 250 microns, preferably between 50 and 250 microns, and more particularly between 100 and 150 microns, in diameter.

It will be understood that certain active ingredients will alone be unable to generate unaided a sufficiently high osmotic potential within the pellet core. For this reason, it is envirsaged that any additional water-soluble ingredients incorporated into the core may purposely be chosen for their ability to enhance the osmotic potential within the core. Typical water-soluble substances which may be included in the core formulation as additional osmotically-active agents include salts such as, for example, NaCl, KCl and/or LiCl; polysaccharides; and polyhydric alcohols such as, for example, sorbitol and/or mannitol.

The pellet core is conveniently prepared by compression or extrusion followed by spheronization using standard techniques as described, for example, in Remington's Pharmaceutical Sciences, 16th Edition, 1980. For use with orally administrable pharmaceuticals, the core preferably measures from 0.5 to 4 mm in diameter since compositions formed with cores greater than 4 mm have a tendency to be retained in the stomach, thereby potentially giving rise to undesirable localized effects as mentioned above. In view of the fact that release of the active ingredient is an osmotically controlled process, the in vivo release rate is essentially independent of the position of the pellet in the gastrointestinal tract, and unaffected by environmental factors such as pH, intestinal mobility and luminal content. The release rate depends solely on the osmolarity and temperature of the environment, both of which show little physiological variation.

For pharmaceutical use, active ingredient(s) which may be incorporated into the core of the pellet of the invention include, for example, drugs affecting the cardiovascular system such as, for example, diuretics, beta-blockers, antihypertensives and/or antiarhythmics e.g. disopyramide, the respiratory system such as, for example, broncho-dilators, steroids, antitussives, systemic decongestants and/or prophylactics of asthma and other allergic disorders and the central nervous system such as, for example, sedatives, anxiolytics, antipsychotics, antidepressants e.g. trazodone, analgesics e.g. morphine and/or antiepileptics, as well as antibiotics, antifungals, hormones such as, for example, cortico-steroids e.g. prednisolone and/or sex hormones, cytotoxics, antagonists used in combating malignant disease and drugs e.g. tiaprofenic acid used in combating rheumatic diseases.

Moreover, for pharmaceutical use the active ingredient(s) in the core may optionally be present in admixture with one or more pharmaceutical carriers and/or excipients. Excipients which facilitate compression or extrusion and spheronization will be of particular benefit and include, by way of example, microcrystalline cellulose, lactose, hydroxy-propylmethylcellulose, mannitol and sucrose.

Furthermore, for pharmaceutical use the multiparticulate compositions of the invention may be in any suitable form conventionally employed in the pharmaceutical art, but will preferably be in the form of a hard gelatin capsule containing a plurality of pellets coated in the manner described above.

The following passage describes illustrative Experiments which were carried out firstly to demonstrate typical methods for preparing the core, and secondly to investigate the release rate of substances from typical compositions placed in various representative media. In the accompanying drawings:

The following abbreviations are employed herein:
HPMC = hydroxypropylmethylcellulose
CA = cellulose acetate
CAP = cellulose acetate propionate
CAB = cellulose acetate butyrate
DBP = dibutyl phthalate
PEG = polyethylene glycol.

The grade of cellulose acetate referred to hereinafter as CA-398-3 is obtainable from Eastman Kodak. The various grades of cellulose acetate propionate (referred to hereinafter as Cellit PR-500, PR-600 and PR-800) and of cellulose acetate butyrate (referred to hereinafter as CAB-500-5) are obtainable from Bayer.

1. PREPARATION OF THE CORE

A. Cores Prepared by Compression

Powder mixes were prepared using osmotically-active compounds and water-soluble dyes to represent the drug, and compressed using 3.2 mm tooling.

Examples:

(i) Potassium chloride and carmosine
(ii) Lithium chloride and tartrazine
(iii) Potassium chloride and methylene blue

B. Cores Prepared by Extrusion

Powder mixes were prepared using osmotically-active compounds, other excipients and water-soluble dyes to represent the drug, by granulation and extrusion. The extrudate was subsequently spheronized and pellets of different diameters were separated (size fractioned).

Examples:

(i) Potassium chloride, Avicel, Lactose, HPMC, Carmosine dye
(ii) Mannitol, Avicel RC 591, HPMC, Carmosine

2. COATING EXERCISES

A 2.0 g sample of the core (1–2 or 2–3 mm size fraction) was placed in a small pan coater and coated using a spray gun. Carmosine release rate was measured by placing 0.5 g samples of the product in dissolution media at various pH values and osmotic pressures.

In the following examples there are described several preferred embodiments to illustrate the invention. However, it is to be understood that the invention is not intended to be limited to the specific embodiments.

EXAMPLE 1

Approximately 1.5 g of potassium chloride pellets (2-3 mm) were coated with 25 ml of a coating solution of the following formulation:

| Material | Quantity |
| --- | --- |
| CA (CA-398-3) | 5 g |
| CAP (Cellit PR-550) | 5 g |
| DBP | 2.5 g |
| Acetone | to 200 ml |

Figure 1:
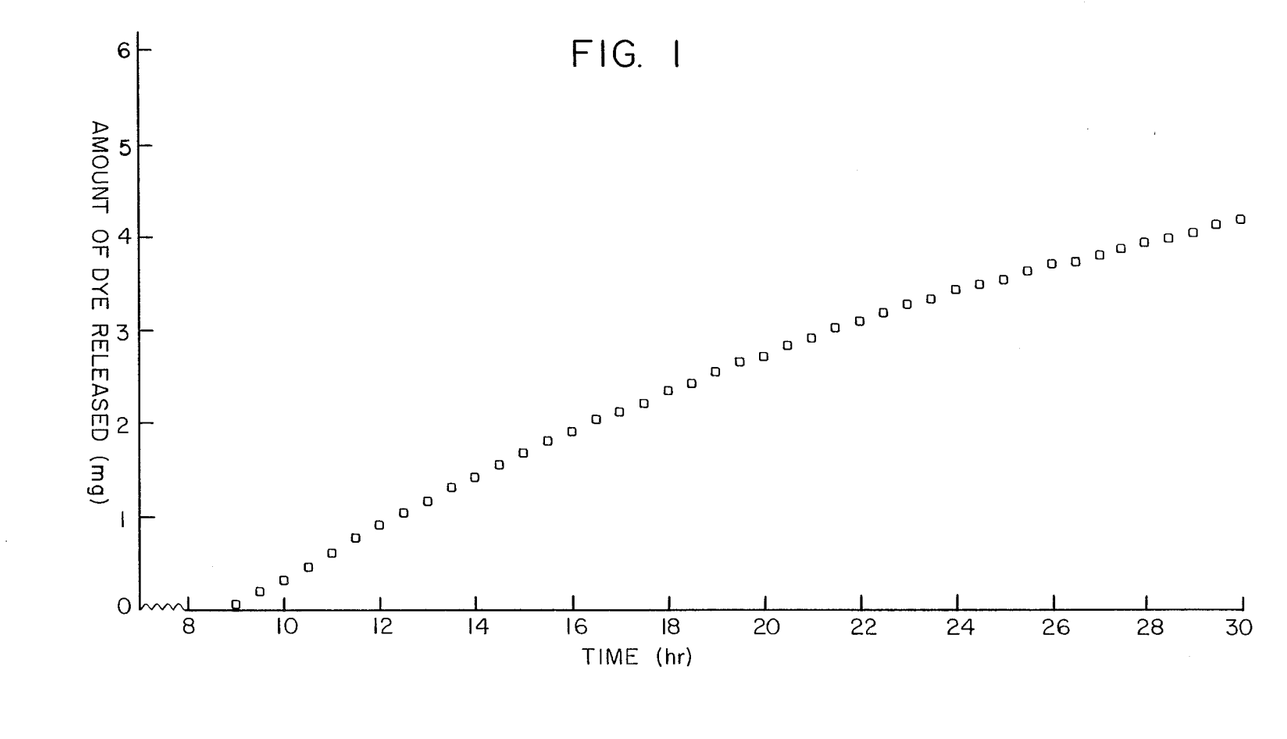
FIGS. 1 and 4 to 8 are graphical representations showing the amount of substance released in mg as a function of time in hours for the compositions of Experiments 1 and 4 to 8 respectively.

The pore-forming agent was 5 mg of caster sugar (125-180 μm size fraction) and the pellets coated well producing a strong and smooth coat. After coating, the weight of the pellets was taken and it was observed that the pellets had increased in weight by 70.4 mg. The pellets were then placed in a medium of 0.9% aqueous sodium chloride. As can be seen from FIG. 1, 50% of the dye was released over 20 hours in an essentially zero-order fashion after a lag time of 9 hours.

EXAMPLE 2

Potassium chloride pellets (2-3 mm in size) were coated with 15 ml of a coating solution, of the following formulation:

| Material | Quantity |
| --- | --- |
| CA (CA-398-3) | 1 g |
| CAP (Cellit PR-500) | 1 g |
| DBP | 0.5 g |
| Acetone | to 40 ml |

Figure 2:
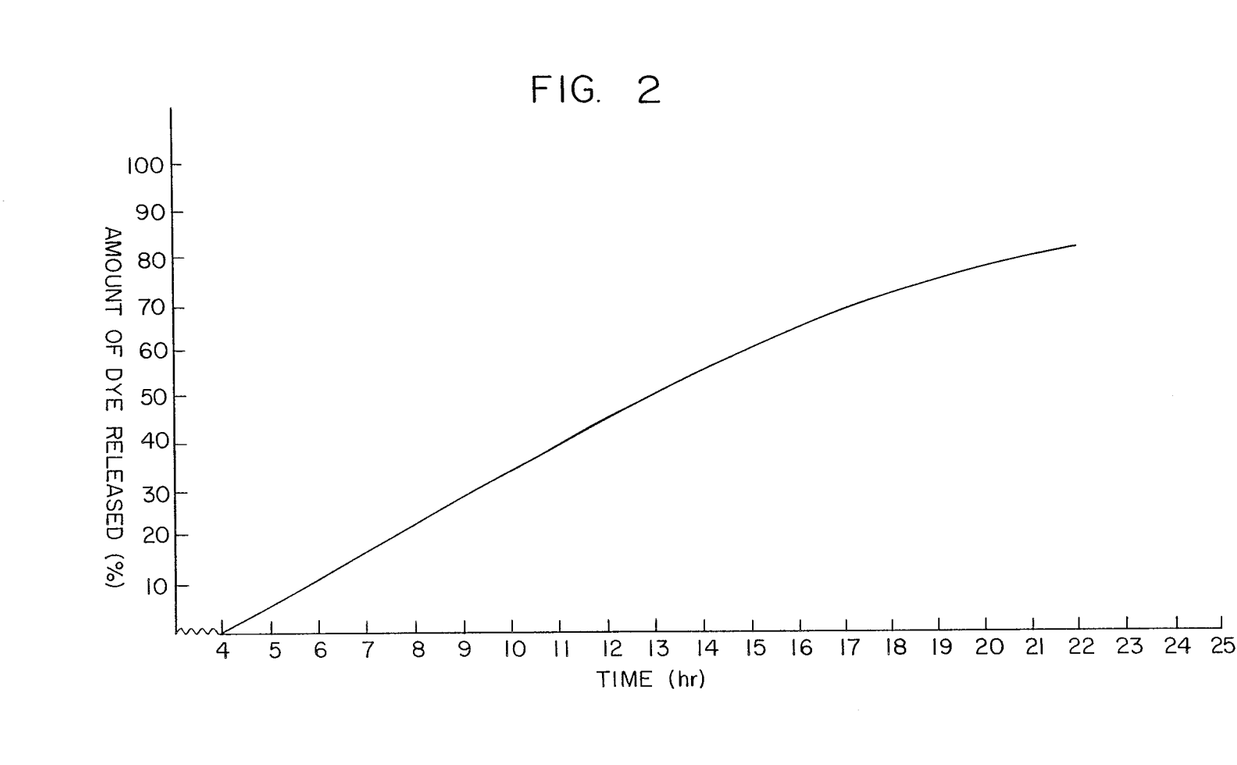
FIGS. 2 and 9 are graphical representations showing the percentage of substance released as a function of time in hours for the compositions of Experiments 2 and 9 respectively.

The pore-forming agent was caster sugar (125-180 μm particle size) and the pellets coated well, producing a smooth and shiny appearance. The pellets were then placed in a medium of distilled water and as can be seen from FIG. 2, 80% of the dye was released over approximately 18 hours after a lag time of approximately 4 hours.

EXAMPLE 3

Figure 3:
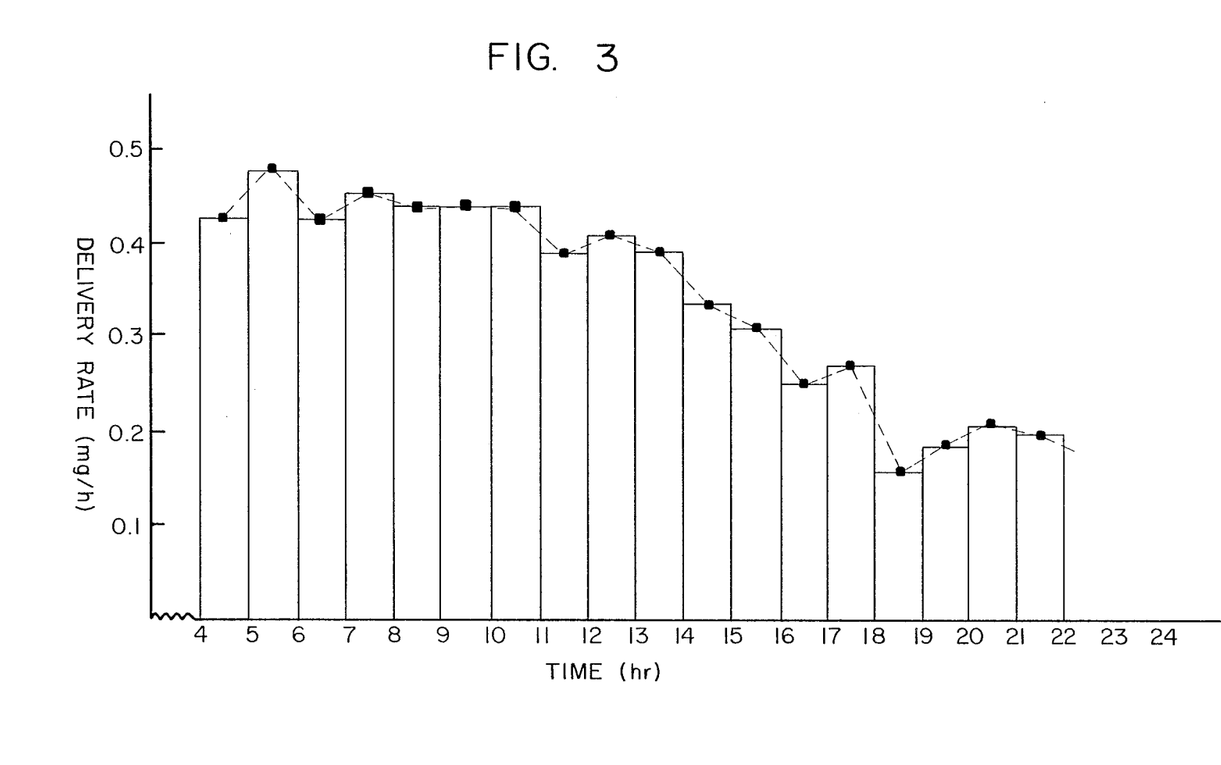
FIG. 3 is a graphical representation plotting the release rate of substance in mg/h as a function of time in hours for the composition of Experiment 3.

FIG. 3 shows the quantity of dye released per hour from the composition of Example 2.

EXAMPLE 4

A comparison between the dissolution rates of pellets coated with different amounts of the same coating solution was undertaken.

| Material | Quantity |
| --- | --- |
| CAP (Cellit PR-800) | 11 g |
| DBP | 2.75 g |
| Acetone | to 220 ml |

Figure 4:
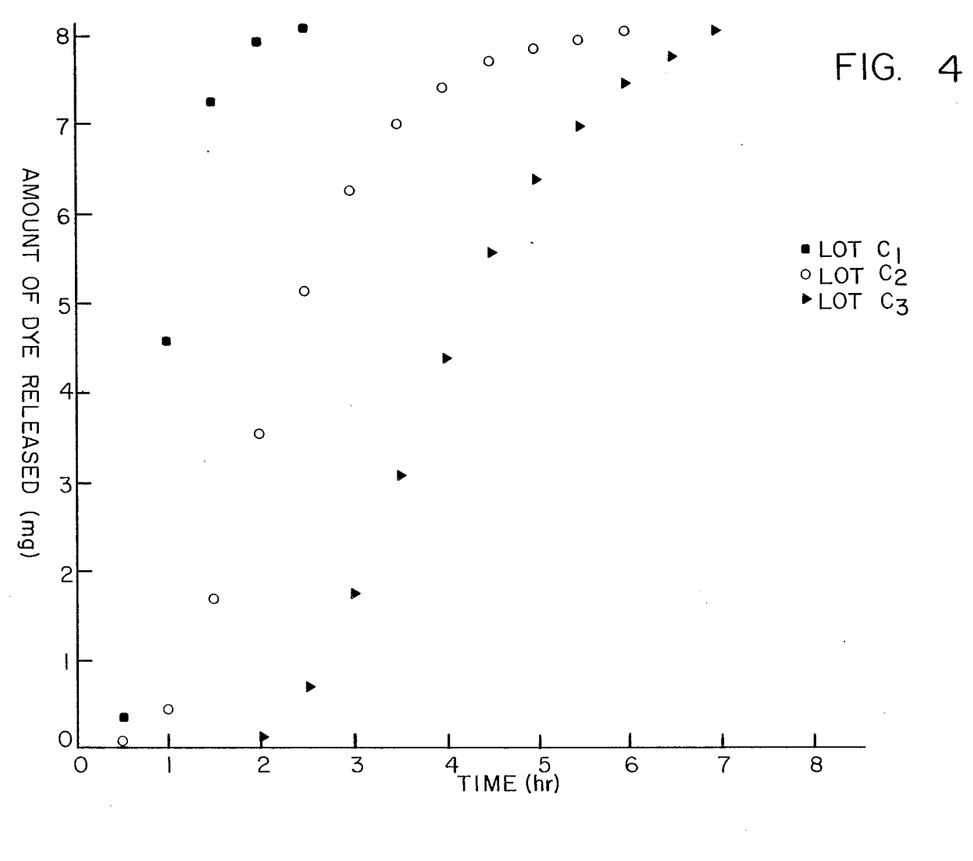

Approximately 2 g of potassium chloride pellets (2-3 mm in size) were used for each coating. Lot C1 (denoted ■ in FIG. 4) was coated with 15 ml of coating solution, lot C2 (denoted 0 in FIG. 4) with 20 ml and lot C3 (denoted ▶ in FIG. 4) with 25 ml. In each case, the pore-forming agent was 5 mg of caster sugar (125-180 μm particle size). The pellets, after coating, had a good appearance although very careful control of the coating conditions was required and the thickness of the coat for each lot was measured. For lot C1, the coat was 20-40 μm in thickness, for lot C2, 40-60 μm and for lot C3, 60-80 μm. The pellets were then placed in a medium of distilled water. As can be seen from FIG. 4, increased coating thickness results in increased release time.

EXAMPLE 5

A comparison between the dissolution rates of pellets coated with different amounts of the same coating solution was undertaken.

| Material | Quantity |
| --- | --- |
| CA (CA-398-3) | 5.25 g |
| CAP (Cellit PR-500) | 5.25 g |
| PEG 400 | 2.63 g |
| Acetone | to 210 ml |

Figure 5:
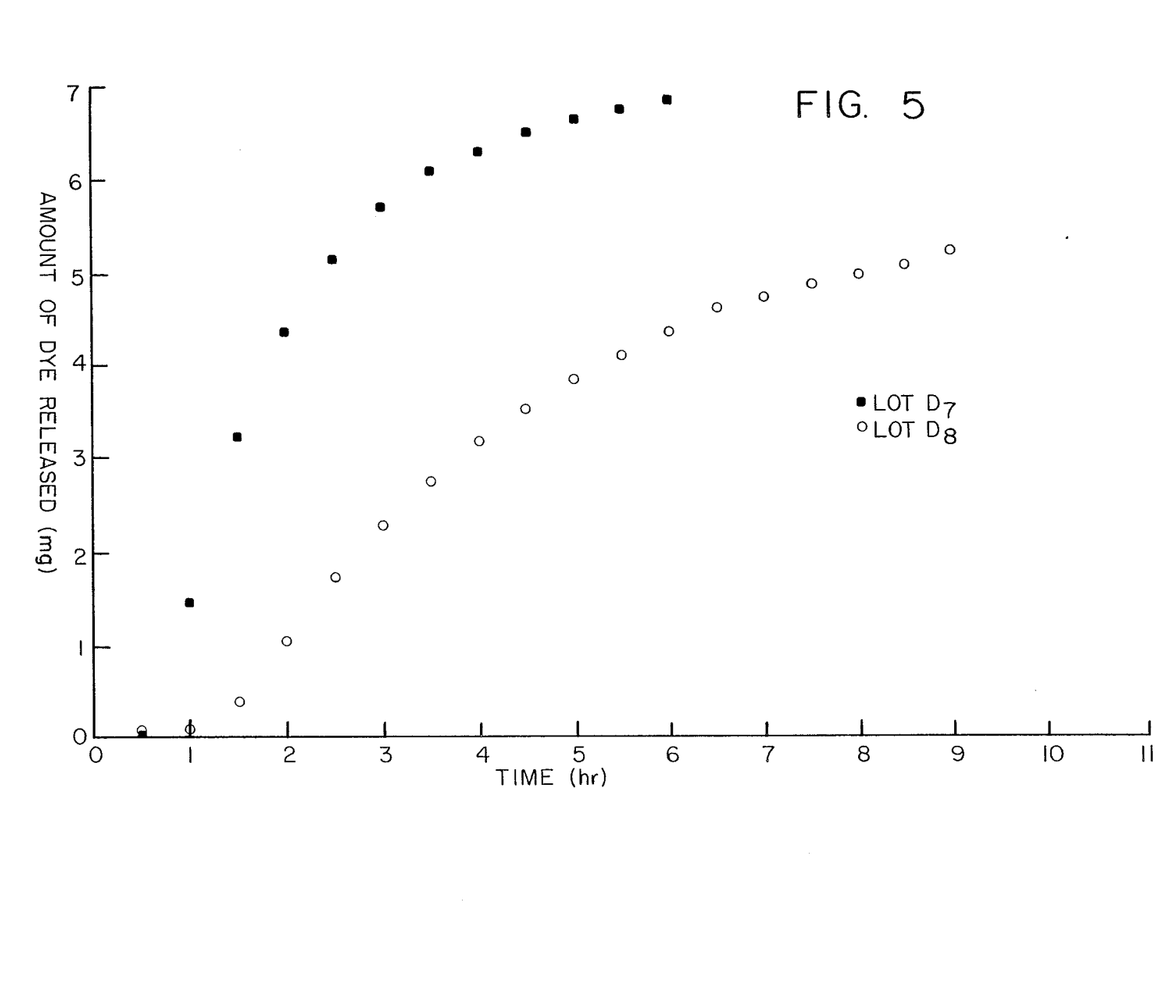

Approximately 2 g of potassium chloride pellets (2-3 mm size fraction) were used for each coating. Lot D7 (denoted ■ in FIG. 5) was coated with 20 ml of coating solution and lot D8 (denoted 0 in FIG. 5) with 25 ml of coating solution. In both cases, the pore-forming agent used was 5 mg of caster sugar (125-180 μm size fraction). The pellets, after coating, had a very good appearance with a strong, smooth and shiny coat and the coated pellets were subsequently weighed. The weight of the coat was 17.2 mg and 28.2 mg for lots D7 and D8, respectively. The pellets were then placed in a medium of isotonic 0.1N HCl. As can be seen from FIG. 5, increased coat thickness resulted in increased release time.

EXAMPLE 6

Example 6 is analogous to Example 5 with the only differences being the formulation of the coating solution and the amount of coat.

| Material | Quantity |
| --- | --- |
| CA (CA-398-3) | 5 g |
| CAP (Cellit PR-600) | 5 g |
| DBP | 2.5 g |
| Acetone | to 200 ml |

Figure 6:
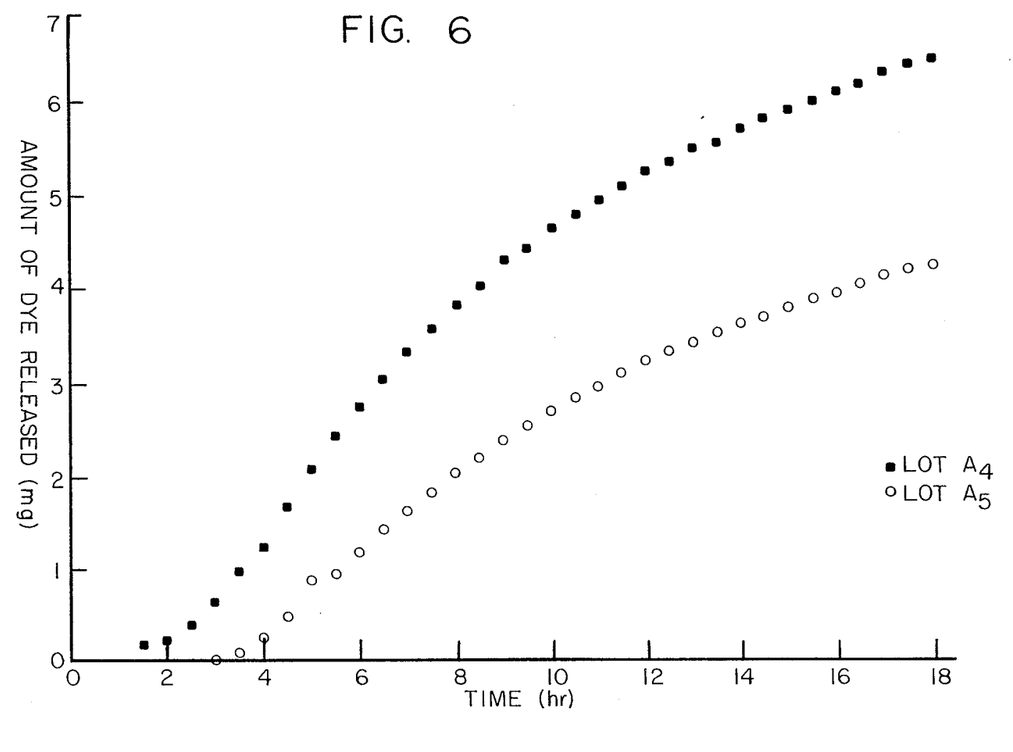

Lot A4 (denoted ■ in FIG. 6) was coated with 15 ml of coating solution and lot A5 (denoted 0 in FIG. 6) with 20 ml of coating solution. In both cases, the pore-forming agent used was 5 mg of caster sugar (90-125 μm particle size). The pellets were weighted after coating and the weight was observed to have increased by 27.4 mg and 46 mg, respectively. The thickness of the coat was measured using a microscope and values of 10-20 μm and 20-30 μm respectively were obtained. The pellets were then placed in a medium of isotonic 0.1N HCl. As can be seen from FIG. 6, increased coat thickness resulted in increased release time.

EXAMPLE 7

A comparison between the dissolution rates of pellets coated with different amounts of coating solution was undertaken.

| Material | Quantity |
| --- | --- |
| CA (CA-398-3) | 5.25 g |
| CAP (Cellit PR-500) | 5.25 g |
| PEG 400 | 2.63 g |
| Acetone | to 210 ml |

Figure 7:
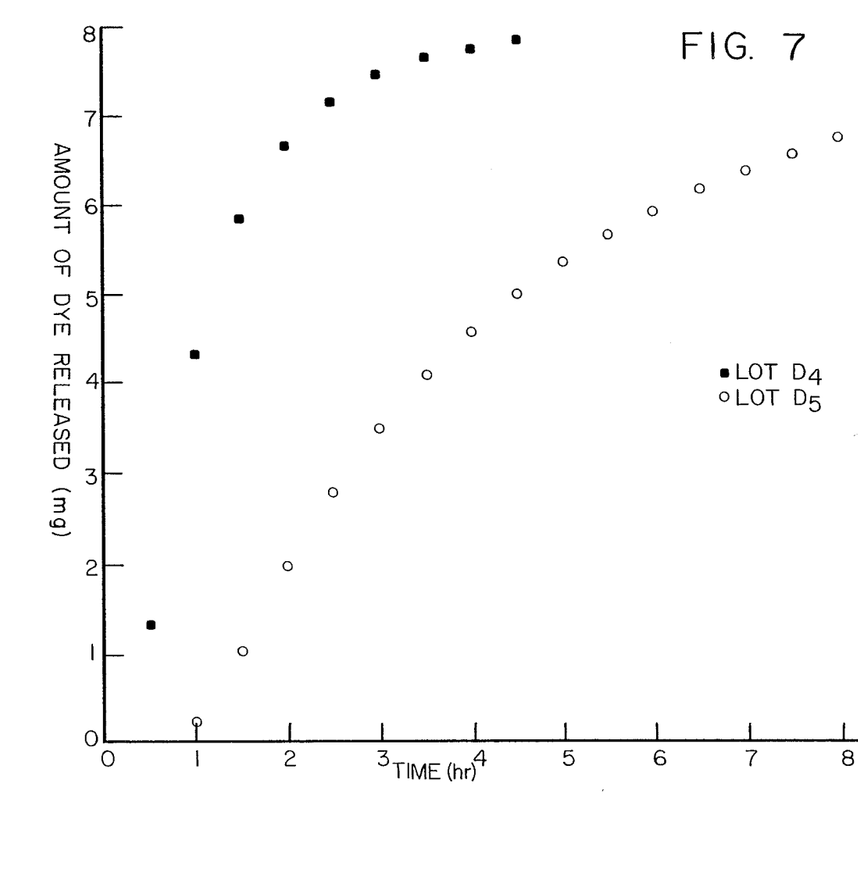

Approximately 2 g of potassium chloride pellets were used for each coating. Lot D4 (denoted ■ in FIG. 7) was coated with 15 ml of coating solution and lot D5 (denoted 0 in FIG. 7) with 20 ml of coating solution. In both cases, the pore-forming agent used was 5 mg of caster sugar (90–125 μm size fraction) and the thicknesses of the coats were 20–40 μm and 60–80 μm for lots D4 and D5 respectively. The pellets were then placed in a medium of 0.9% aqueous sodium chloride. As can be seen from FIG. 7, increased coat thickness resulted in increased release time.

EXAMPLE 8

A comparison between the dissolution rates of one batch of pellets in two different media was undertaken.

| Material | Quantity |
| --- | --- |
| CA (CA 398-3) | 11 g |
| PEG 400 | 2.75 g |
| DBP | 2.75 g |
| Acetone | to 220 ml |

Figure 8:
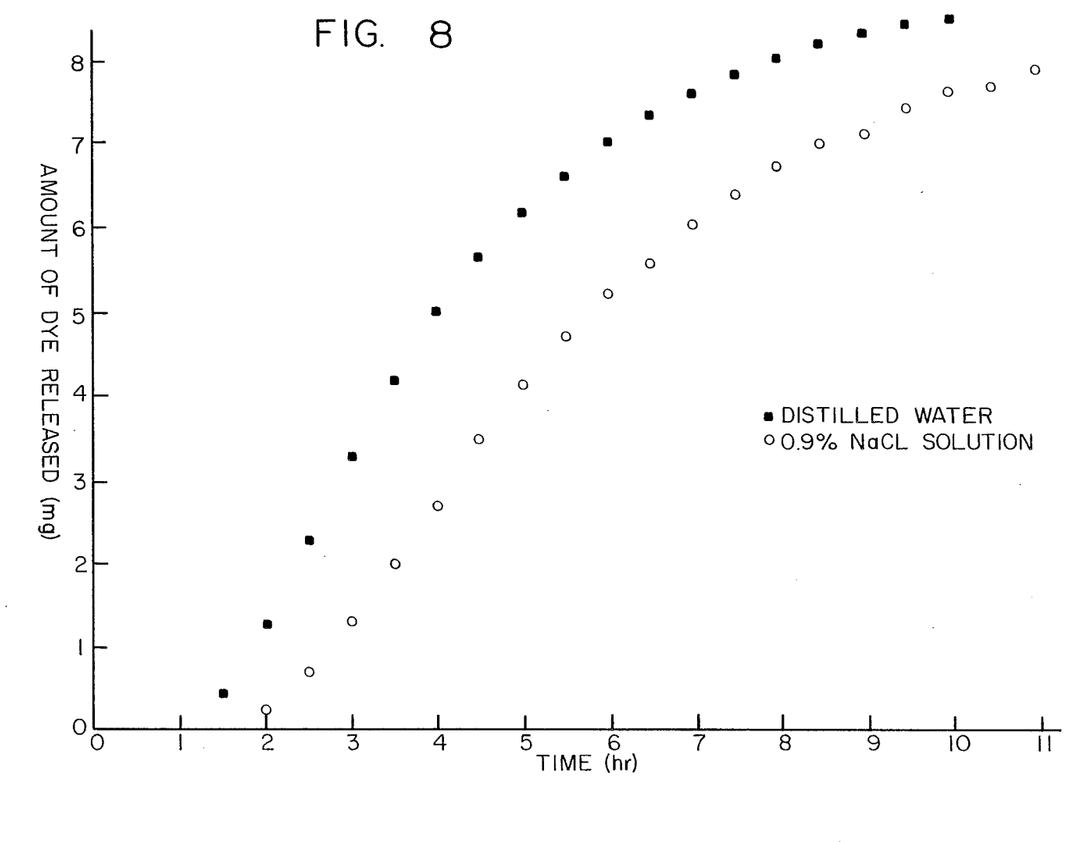

2 g of potassium chloride pellets were coated with 25 ml of the above coating solution and the pore-forming agent used was 5 mg of caster sugar (125–180 μm size fraction). Dissolution testing was carried out in distilled water (denoted ■ in FIG. 8) and 0.9% sodium chloride solution (denoted 0 in FIG. 8). As can be seen from FIG. 8, a reduced release rate is observed with an increase in osmotic pressure.

EXAMPLE 9

2 g of potassium chloride pellets were coated with 25 ml of coating solution of the following formulation:

| Material | Quantity |
| --- | --- |
| CA (CA-398-3) | 2.5 g |
| CAB (CAB-500-5) | 2.5 g |
| DBP | 1.25 g |
| Acetone | to 100 ml |

Figure 9:
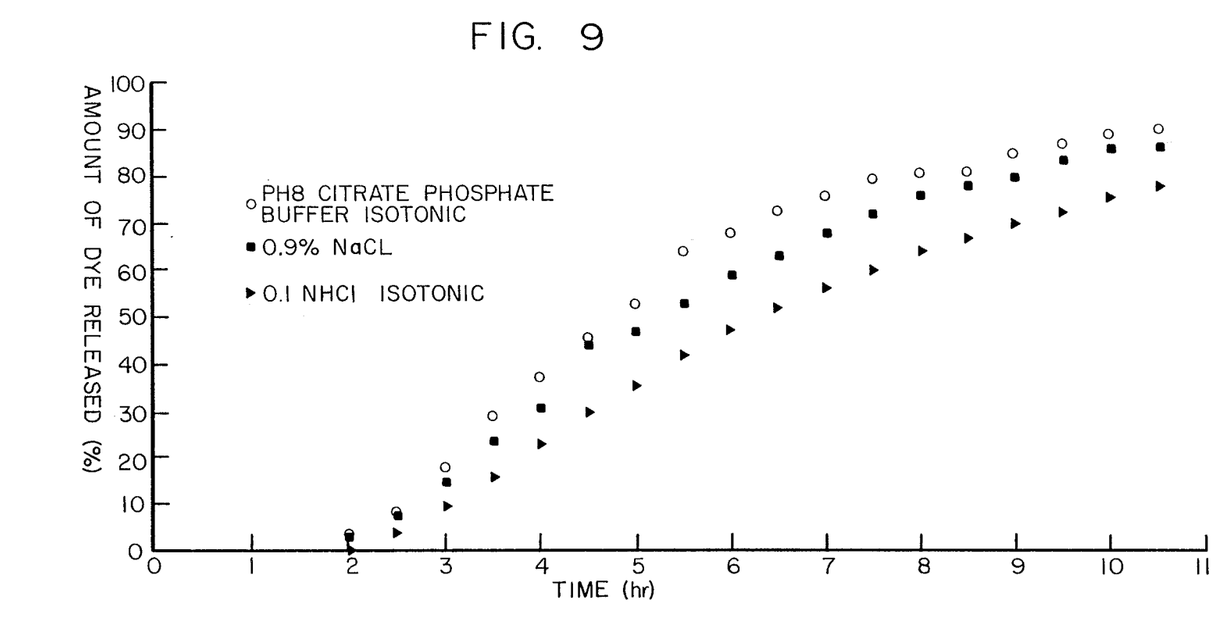

The release rate in media at various pH values was examined. The media chosen were 0.9% aqueous sodium chloride (denoted ■ in FIG. 9), isotonic citrate-phosphate pH 8 buffer (denoted 0 in FIG. 9) and isotonic 0.1N HCl (denoted ▶ in FIG. 9). As can be seen from FIG. 9, release rate is essentially independent of pH at pH values between 1 and 8.

EXAMPLE 10

Compositions incorporating trazodone hydrochloride

Trazodone hydrochloride pellets were prepared using sodium chloride, Avicel PH-101, lactose (200 mesh) and HPMC as excipients and pellets of 2–3 mm diameter were used for coating. A 2.0 g portion of the pellets was placed in the coating pan and 5 mg of 125–180 μm sugar particles were suspended in 15 ml of coating solution (CA-398-3, Cellit PR-500, DBP) and the pellets were coated with the above solution.

Dissolution testing was carried out on 600 mg of the pellets (equivalent to 28.0 mg of trazodone hydrochloride) in phosphate-citrate buffer of pH 6.0. As can be seen from the following results, approximately 80% of the active ingredient was released in zero-order rate over 4 hours.

| Time (h) | Amount of active ingredient released (%) |
| --- | --- |
| 0.5 | 1.1 |
| 1.0 | 5.1 |
| 1.5 | 15.5 |
| 2.0 | 32.5 |
| 2.5 | 50.5 |
| 3.0 | 66.1 |
| 3.5 | 77.3 |
| 4.0 | 84.1 |
| 4.5 | 89.5 |
| 5.0 | 93.5 |
| 5.5 | 95.6 |
| 6.0 | 97.5 |
| 6.5 | 98.6 |
| 7.0 | 99.6 |

EXAMPLE 11

Compositions incorporating morphine sulfate

Morphine sulfate pellets were prepared using sodium chloride, Avicel PH-101, lactose (200 mesh) and HPMC as excipients and pellets of 1.4–2.0 mm diameter were used for coating. A 2.0 g portion of the pellets was placed in the coating pan and 5 mg of 125–180 μm sugar particles suspended in 25 ml of coating solution (CA-398-3, Cellit PR-500, DBP) and the pellets were coated with 25 ml of the above solution.

Dissolution testing was carried out on 850 mg of the pellets (equivalent to 16.7 mg of morphine sulfate) in 0.001N HCl. As can be seen from the following results, approximately 10 mg (60%) of active ingredient was released in zero-order rate over 20 hours.

| Time | Amount of active ingredient released (mg) |
| --- | --- |
| 0.5 | — |
| 2.0 | 1.350 |
| 4.0 | 2.925 |
| 6.0 | 4.500 |
| 8.0 | 5.625 |
| 10.0 | 6.525 |
| 12.0 | 7.200 |
| 14.0 | 7.650 |
| 16.0 | 8.325 |
| 18.0 | 9.450 |
| 19.0 | 9.900 |

EXAMPLE 12

Compositions incorporating prednisolone

Prednisolone pellets were prepared using sodium chloride, Avicel PH-101, lactose (200 mesh) and HPMC as excipients and pellets of 2–3 mm diameter were used for coating. A 2.0 g portion of the pellets was placed in a coating pan and sprayed with 25 ml of coating solution (the coating formulation was exactly as for the morphine sulfate pellets of Example 2).

Dissolution testing was carried out on 600 mg of the pellets (equivalent to 11.8 mg of prednisolone). As can be seen from the following results, approximately 66% of the active ingredient was released in zero-order rate over 40 hours in 0.1N HCl.

| Time (h) | Amount of ingredient released (mg) |
| --- | --- |
| 0 | — |
| 4.0 | 0.52 |
| 8.0 | 1.35 |
| 12.0 | 2.22 |
| 16.0 | 3.08 |
| 20.0 | 3.92 |
| 24.0 | 4.72 |
| 28.0 | 5.53 |
| 32.0 | 6.33 |
| 36.0 | 7.08 |
| 40.0 | 7.83 |

EXAMPLE 13

Compositions incorporating tiaprofenic acid

Tiaprofenic acid pellets were prepared using the same excipients as those used for the prednisolone pellets of Example 13 and a dose of 600 mg contains 268 mg of tiaprofenic acid. Pellets of 2-3 mm diameter were used for coating exercises and a 2.0 g portion of the pellets was coated with 25 ml of coating solution (the formulation and size of the sugar particles were as in the previous Examples).

Dissolution testing was carried out on 600 mg of the pellets in 900 ml of citrate buffer, pH 5.5. As can be seen from the following results, the composition exhibited a 40-hour release pattern in zero-order rate in the above medium.

| Time (h) | Amount of active ingredient released (mg) |
| --- | --- |
| 0 | — |
| 4.0 | 25.53 |
| 8.0 | 48.14 |
| 12.0 | 68.86 |
| 16.0 | 86.44 |
| 20.0 | 103.81 |
| 24.0 | 120.14 |
| 28.0 | 134.58 |
| 32.0 | 148.19 |
| 36.0 | 160.54 |
| 40.0 | 172.05 |

EXAMPLE 14

Compositions incorporating disopyramide phosphate

Disopyramide phosphate pellets were prepared using the same excipients as those used for the prednisolone pellets of Example 13 and a 470 mg dose contains 250 mg of disopyramide phosphate (193 mg base). Pellets of 2-3 mm diameter were used for coating exercises and a 2.0 g portion of the pellets was coated with 25 ml of coating solution (the formulation and size of the sugar particles were as in the previous Examples).

Dissolution testing was carried out on 400 mg of the pellets in 900 ml of 0.001N HCl. As can be seen from the following results, 70% of the active ingredient was released in zero-order rate over 12 hours.

| Time (h) | Amount of active ingredient released (%) |
| --- | --- |
| 0 | — |
| 2.0 | 6.1 |
| 4.0 | 24.4 |
| 6.0 | 46.2 |
| 8.0 | 59.4 |
| 10.0 | 68.5 |
| 12.0 | 75.2 |
| 14.0 | 80.7 |
| 16.0 | 84.9 |
| 18.0 | 87.8 |
| 20.0 | 90.8 |

Various modifications of the compositions and method of the invention may be made without departing from the spirit or scope thereof and it is to be understood that the invention is intended to be limited only as defined in the appended claims.

What is claimed is:

1. A controlled release means comprising a core of at least one water-soluble ingredient selected from the group consisting of drugs affecting the cardiovascular system, for the respiratory system, and for the central nervous system, antibiotics, antifungals, hormones, cytotoxics, antagonists used in combating malignant disease and drugs used in combating rheumatic diseases of which at least one ingredient is to be released in a controlled manner, said core being surrounded by a semi-permeable membrane polymer coating containing dispersed water-soluble pore-forming particles in sufficient amount to give rise to dissolution upon exposure to an aqueous environment to form one or two pores with a diameter of 50 to 250 microns extending through the coating to provide communication between the core and the exterior of the coating material the weight ratio of pore-forming particles to coating being 1 to 40 to 1 to 6,000.

2. The means of claim 1 in pellet form.

3. The means of claim 2 wherein the proportion by weight of pore-forming particles to coating material in the pellet is between 1 to 40 and 1 to 6000.

4. The means of claim 3 wherein the proportion by weight of pore-forming particles to coating material in the pellet is about 1 to 300.

5. The means of claim 1 wherein the diameter(s) of the pore-forming particle(s) exceeds the thickness of the semi-permeable membrane coat.

6. A method of preparing the controlled-release means of claim 1 comprising coating a core of at least one water-soluble ingredient selected from the group consisting of drugs affecting the cardiovascular system, for the respiratory system, and for the central nervous system, antibiotics, antifungals, hormones, cytotoxics, antagonists used in combating malignant disease and drugs used in combating rheumatic diseases of which at least one ingredient is to be released in a controlled manner with a semi-permeable polymer membrane in the presence of water-soluble, pore-forming particles to form a membrane coating with the particles dispersed therein in a sufficient amount to give rise through dissolution to one or two pores with a diameter of 50 to 250 microns formed upon exposure to an aqueous environment for communicate with the core and the outer environment material the weight ratio of pore-forming particles to coating being 1 to 40 to 1 to 6,000.

7. A multiparticulate controlled-release composition comprising a plurality of the means of claim 1.

* * * * *